(12) United States Patent
Nakahara et al.

(10) Patent No.: US 6,348,135 B1
(45) Date of Patent: Feb. 19, 2002

(54) PROCESS FOR THE PURIFICATION OF (METH) ACRYLIC ACID AND/OR ITS ESTER

(75) Inventors: Sei Nakahara, Himeji; Yukihiro Matsumoto, Kobe; Masatoshi Ueoka, Himeji, all of (JP)

(73) Assignee: Nippon Shokubai Co., Ltd., Osaka-Fu (JP)

( * ) Notice: Subject to any disclaimer, the term of this patent is extended or adjusted under 35 U.S.C. 154(b) by 0 days.

(21) Appl. No.: 09/521,434

(22) Filed: Mar. 8, 2000

(30) Foreign Application Priority Data

Mar. 9, 1999 (JP) .......................................... 11-062265

(51) Int. Cl.$^7$ .............................. B01D 3/34; C07C 51/44
(52) U.S. Cl. ............................... 203/8; 203/49; 203/98; 203/DIG. 21; 203/DIG. 25; 562/600
(58) Field of Search ........................ 203/49.8, DIG. 21, 203/DIG. 25, 98; 562/600; 159/901, 16.1, DIG. 10

(56) References Cited

U.S. PATENT DOCUMENTS

| | | | | |
|---|---|---|---|---|
| 3,280,010 A | * | 10/1966 | Creighton et al. | ............ 203/95 |
| 3,674,651 A | | 7/1972 | Otsuki et al. | ................. 203/8 |
| 4,021,310 A | | 5/1977 | Shimizu et al. | ................ 203/8 |
| 4,260,821 A | * | 4/1981 | Benjamin | ..................... 203/8 |
| 4,263,448 A | * | 4/1981 | Leacock | ..................... 560/246 |
| 4,365,081 A | * | 12/1982 | Shimizu et al. | ................. 203/6 |
| 4,490,215 A | * | 12/1984 | Bannon | ..................... 202/153 |
| 5,330,624 A | * | 7/1994 | Ebert | ......................... 203/98 |
| 5,441,605 A | * | 8/1995 | Beasley et al. | ............. 203/100 |

FOREIGN PATENT DOCUMENTS

DE    2 362 373    7/1974

OTHER PUBLICATIONS

Database WPI, Section Ch, Week 199517, Derwent Publications Ltd., London, GB; Class A41, An 1995–128282 XP002141956 & JP 07 053449 A (Mitsibishi Petrochemical Co., Ltd.), Feb. 28, 1995 * Abstract*.

* cited by examiner

Primary Examiner—Virginia Manoharan
(74) Attorney, Agent, or Firm—Wenderoth, Lind & Ponack, L.L.P.

(57) ABSTRACT

In a process for the purification of (meth)acrylic acid and/or its ester using a distillation unit containing a distillation column, a multitubular reboiler and a pipe connecting these elements, an oxygen containing gas is supplied from a least one point in regions between the distillation column and an inlet of the multitubular reboiler and/or in regions between the inlet and an inlet side tube sheet of the multitubular reboiler. This process can effectively prevent the formation of polymerization products and can stably purify (meth) acrylic acid and/or its ester over a long time.

14 Claims, 5 Drawing Sheets

OXYGEN CONTAINING GAS SUPPLY NOZZLE 22
23 GAS OUTLET HOLE
23

PROCESS FOR THE PURIFICATION OF (METH) ACRYLIC ACID AND/OR ITS ESTER

This application is based on patent application No. 11-62265 filed in Japan, the contents of which are hereby incorporated by references.

BACKGROUND OF THE INVENTION

1. Field of the Invention

The present invention relates to a process for the purification of (meth)acrylic acid and/or its ester. Specifically, the present invention relates to a process for the purification of (meth)acrylic acid and/or its ester using a distillation unit comprising a distillation column, a multitubular reboiler, and a pipe connecting the distillation column with the reboiler, which process is capable of preventing the formation of polymerization products in the reboiler and is capable of stably purifying (meth)acrylic acid and/or its ester over a long time.

2. Description of the Related Art

In commercial purification of (meth)acrylic acid and/or its ester, a liquid mixture containing (meth)acrylic acid and/or its ester is generally distilled to separate higher boiling components and lower boiling components contained in the liquid mixture by using a distillation unit including a distillation column, a multitubular reboiler, and a pipe connecting these elements.

Such (meth)acrylic acid and its esters are easily polymerized during the purification process, and it is difficult to prevent polymerization of these compounds in a distillation column for a long time. To this end, Japanese Examined Patent Publications No. 52-34606 and No. 57-61015 each disclose the introduction of a gaseous oxygen from the bottom of a distillation column.

According to the processes disclosed in the above publications, however, although the formation of polymerization product in the distillation column can be avoided, polymerization products form inside the connecting pipe and especially inside tubes constituting the multitubular reboiler which cause clogging of tubes to block the distillation from continuing the purification process.

Accordingly, an object of the invention is to provide a process for the purification of (meth)acrylic acid and/or its ester using a distillation unit comprising a distillation column, a multitubular reboiler, and a pipe connecting these elements, which process is capable of effectively preventing the formation of polymerization products in the reboiler and is capable of stably purifying (meth)acrylic acid and/or its ester over a long time.

SUMMARY OF THE INVENTION

After intensive investigations, the present inventors found a process which is capable of preventing the formation of polymerization products in the reboiler and is capable of stably purifying (meth)acrylic acid and/or its ester over a long time.

Such a process is a process for the purification of (meth)acrylic acid and/or its ester using a distillation unit, said distillation unit comprising a distillation column, a multitubular reboiler, and a pipe connecting the distillation column with the multitubular reboiler, wherein an oxygen containing gas is supplied from at least one point in regions between the distillation column and an inlet of the reboiler and/or in regions between the inlet and an inlet side tube sheet of the multitubular reboiler.

DESCRIPTION OF THE PREFERRED EMBODIMENT

The present inventive method is preferably applied to a process for the purification of (meth)acrylic acid and/or its ester using a distillation unit, said distillation unit including a distillation column, a multitubular reboiler, and a pipe connecting these elements.

Esters of (meth)acrylic acid (i.e., acrylic acid and methacrylic acid) to be purified according to the invention include, but are not limited to, methyl (meth)acrylate, ethyl (meth)acrylate, butyl (meth)acrylate, 2-ethylhexyl (meth)acrylate, cyclohexyl (meth)acrylate, and other alkyl esters; hydroxyethyl (meth)acrylate, hydroxypropyl (meth)acrylate, and other hydroxyalkyl esters; dimethylaminoethyl (meth)acrylate, diethylaminoethyl (meth)acrylate, and other dialkylamino-substituted alkyl esters; and methoxyethyl (meth)acrylate, ethoxyethyl (meth)acrylate, and other alkoxy-substituted alkyl esters.

A multitubular reboiler employed in the invention is a means for providing heat to the distillation column by taking a portion of liquid at the bottom of a distillation column (hereinafter may be referred to as "the bottoms") and passing the bottoms through the reboiler to add heat by a heating medium and then the heated bottoms back to the distillation column.

The types of the multitubular reboiler for use in the present invention include, but are not limited to, natural circulation type of vertical or horizontal multitubular reboilers, forced circulation type of vertical or horizontal multitubular reboilers which pass the bottoms through inside constitutive tubes for heat exchange.

Figure 1:
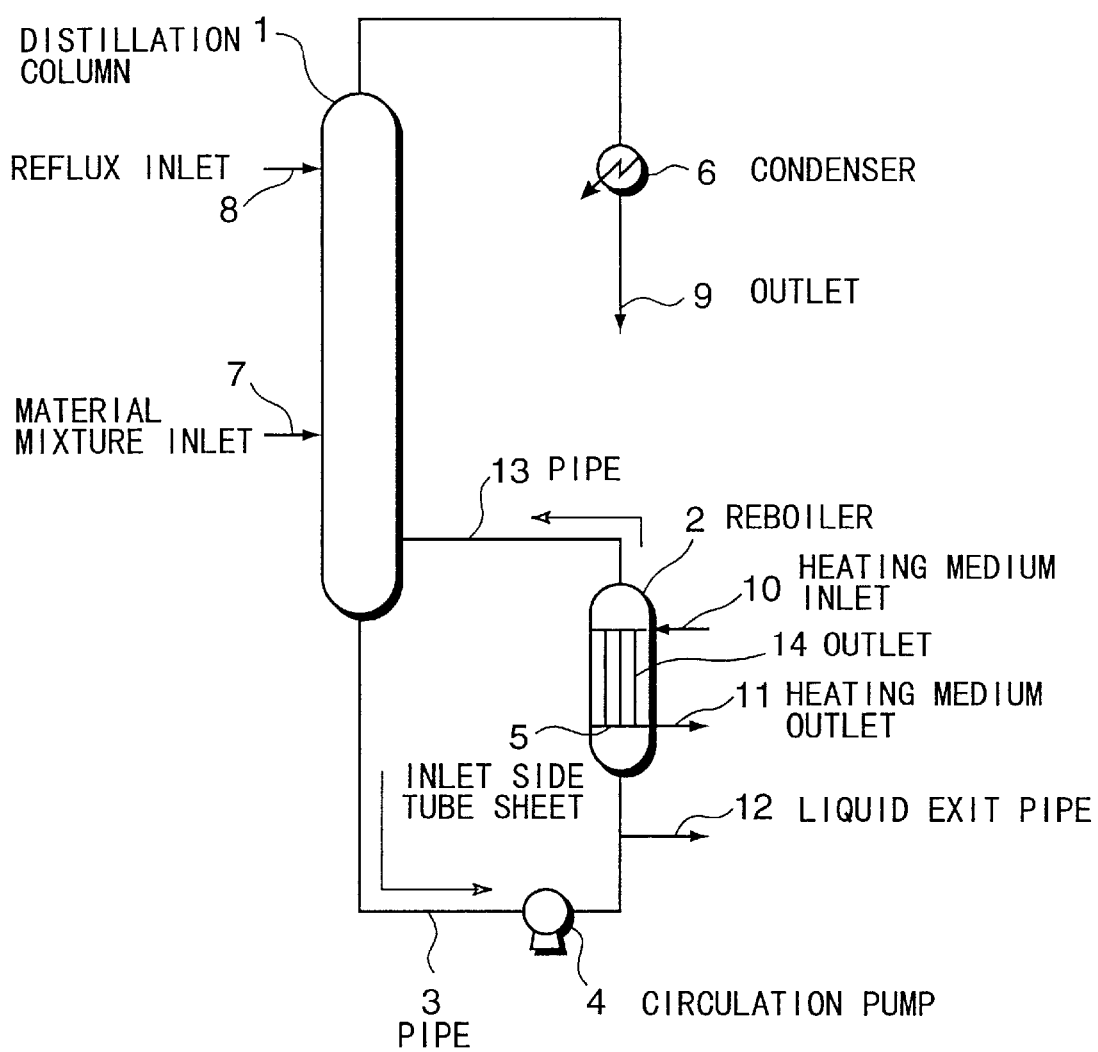
FIG. 1 is a schematic diagram of an embodiment of a distillation unit for use in the present invention.

The present invention will be further illustrated with reference to FIG. 1, which is a schematic diagram of an embodiment of a distillation unit for use in the invention. It should be noted that FIG. 1 through FIG. 8 are just an example of an apparatus usable in the method of the present invention, and the present invention does not necessarily use these apparatus.

The distillation unit includes a distillation column 1, a vertical multitubular reboiler 2, a pipe 3 connecting the bottom of the distillation column 1 with an inlet of the reboiler 2 and a pipe 13 connecting an outlet of the reboiler 2 and the distillation column 1. The pipe 3 may be connected at the bottom or at the side wall of the distillation column 1 such as shown FIG. 7.

A liquid mixture containing (meth)acrylic acid and/or its ester to be purified is fed from an material mixture inlet 7 into the distillation column 1 and is subjected to distillation, and the bottoms from the distillation column 1 is introduced through the pipe 3 into the reboiler 2, and is heated by a heating medium which is introduced into the reboiler 2 from the heating medium inlet 10, and the heated bottoms is fed back to the distillation column 1 through a pipe 13.

A circulation pump 4 for pumping the bottoms into the reboiler 2 may be installed at an optional point between the distillation column 1 and the inlet of the multitubular reboiler 2.

A liquid exit pipe 12 may be connected at an optional point of the pipe 3 to extract a part of the bottoms.

According to the invention, an oxygen source such as gaseous oxygen source including air and an oxygen gas and the like (hereinafter may be referred to as "oxygen containing gas") is supplied from at least one point in regions between the distillation column 1 and the inlet of the multitubular reboiler 2 (for example, at least one point in regions of the pipe 3) and/or in regions between an inlet and an inlet side tube sheet of the multitubular reboiler 2.

By this configuration, the formation of polymerization products inside the tubes of the reboiler 2 can be effectively prevented and the stable purification of (meth)acrylic acid and/or its ester is attained.

Preferably air, more preferably oxygen gas is employed as the oxygen containing gas. Also an oxygen containing exhaust gas discharged from other process such as a vacuum pump, from a ejector and the like can be reusable as the oxygen containing gas of this inventive method.

When the circulation pump 4 is installed, the oxygen containing gas should be preferably supplied from a point between an outlet of the circulation pump 4 and the inlet side tube sheet of the reboiler 2 to avoid the cavitation of the pump 4.

When the liquid exit pipe 12 is connected to the pipe 3 and the oxygen containing gas is supplied from the upstream of a branch point 30, a part of the oxygen containing gas flows through the liquid exit pipe 12 with the part of bottoms. To avoid such a loss of the oxygen containing gas, supplying the oxygen containing gas from the downstream of the branch point 30 is recommended, or supplying the enough oxygen containing gas to cover the loss of the oxygen containing gas from the liquid exit pipe 12.

The proportion of the oxygen containing gas (in terms of oxygen) to be supplied is usually from 0.01 to 5 parts by volume and preferably from 0.02 to 3 parts by volume relative to the 100 parts by volume at standard temperature and pressure of a vapor evolved in the reboiler 2. If the proportion is less than 0.01 parts by volume, the polymerization cannot be sufficiently prevented. In contrast, if the proportion exceeds 5 parts by volume, the amount of active components accompanied by the oxygen gas or oxygen containing gas is increased. In addition, a unit for reducing the pressure is to have an excessive capacity when the distillation is performed under reduced pressure.

Figure 3:
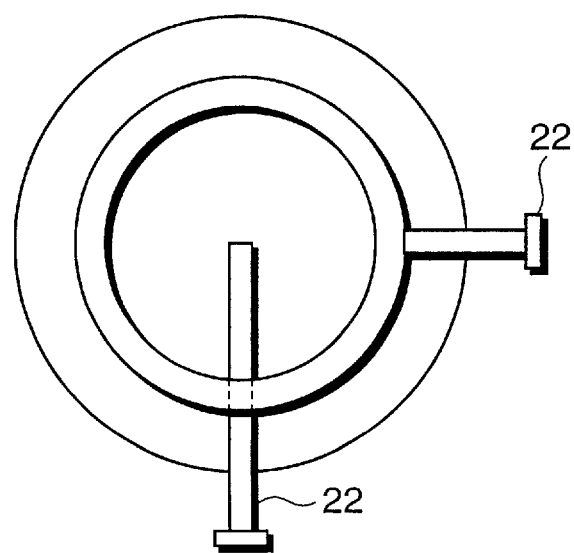
FIG. 3 is a horizontal cross-sectional view of a vertical multitubular reboiler and an oxygen containing gas supply nozzles for use in the present invention.
Figure 4:
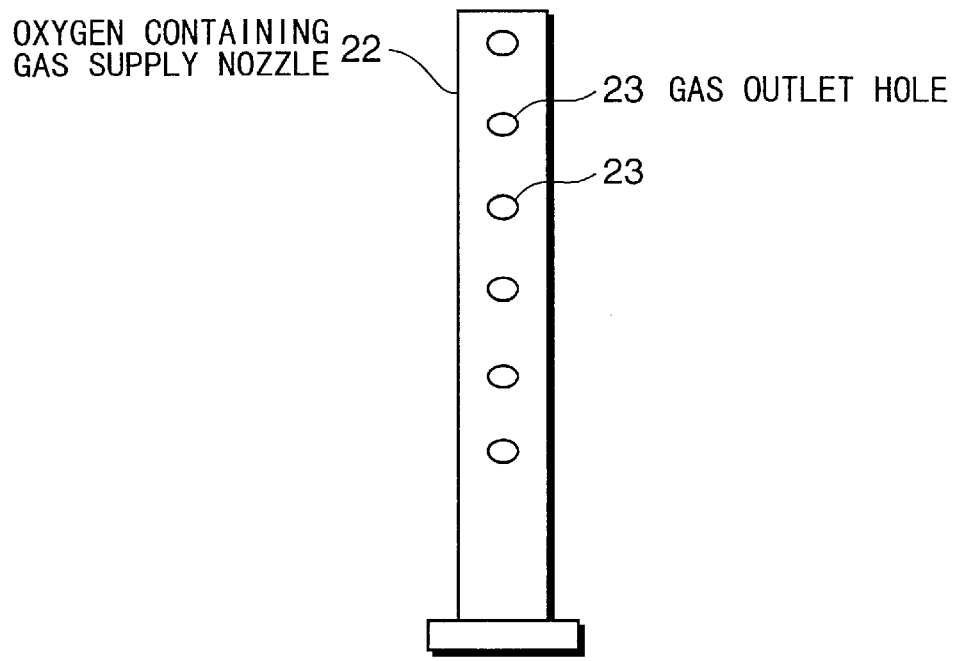
FIG. 4 is a schematic drawing of an oxygen containing gas supply nozzle view from the above.
Figure 5:
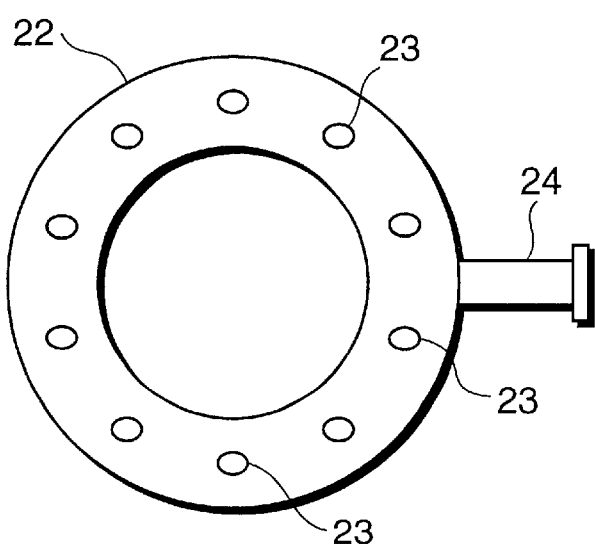
FIG. 5 is a schematic drawing of a ring shaped oxygen containing supply nozzle view from the above.

According to the present invention, the supply means of the oxygen containing gas into the pipe include, but are not limited to, a nozzle with/without a gas outlet hole(s) 23 such as shown in FIG. 4, ring shaped pipe with/without the hole(s) 23 such as shown in FIG. 5 and the combination of the ring shaped pipe and the nozzle(s) such as shown in FIG. 3. With the hole(s) on the body of the nozzle or the pipe, more uniform dispersion of the oxygen containing gas into a pipe or a tube which is connecting the distillation column 1 and the reboiler 2 such as the pipe 3, and into the reboiler 2 such as the inlet side tube sheet 5 is attained.

Figure 2:
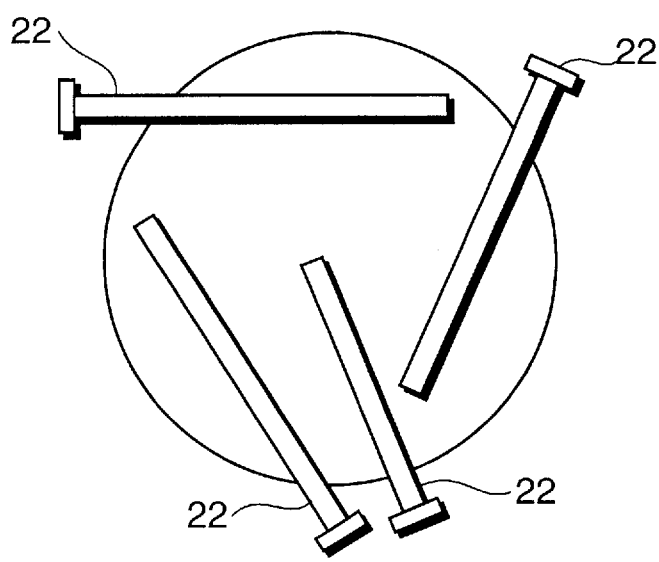
FIG. 2 is a horizontal cross-sectional view of a vertical multitubular reboiler and an oxygen containing gas supply nozzles for use in the present invention.
Figure 6:
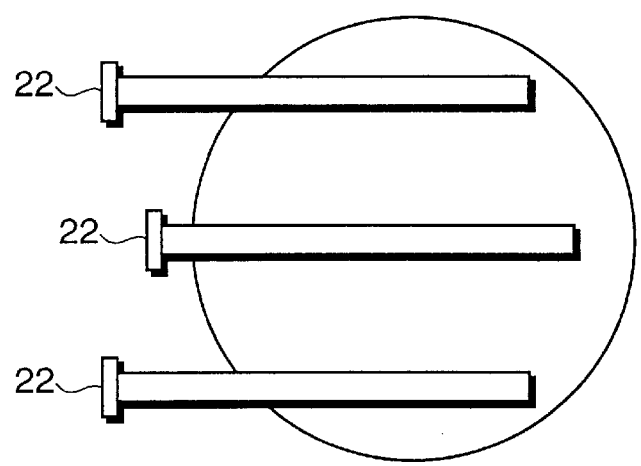
FIG. 6 is horizontal cross sectional view of a horizontal multitubular reboiler and oxygen containing supply nozzles for use in the present invention.
Figure 7:
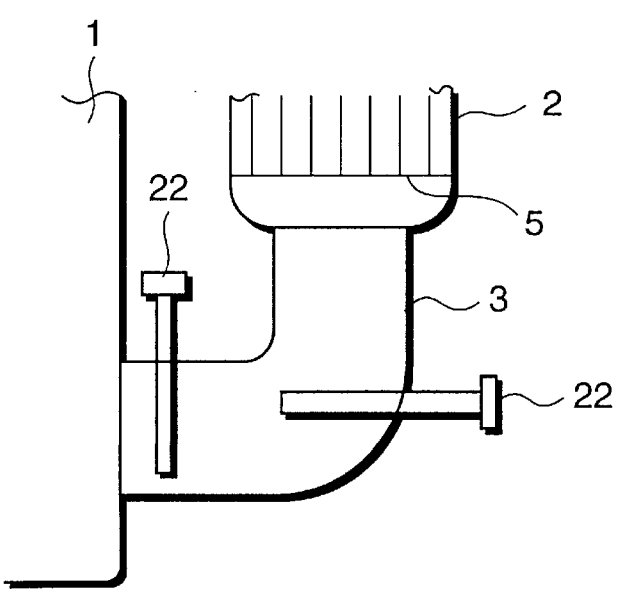
FIG. 7 is a vertical cross sectional view of a pipe 3 and oxygen containing supply nozzles and a part of a reboiler.
Figure 8:
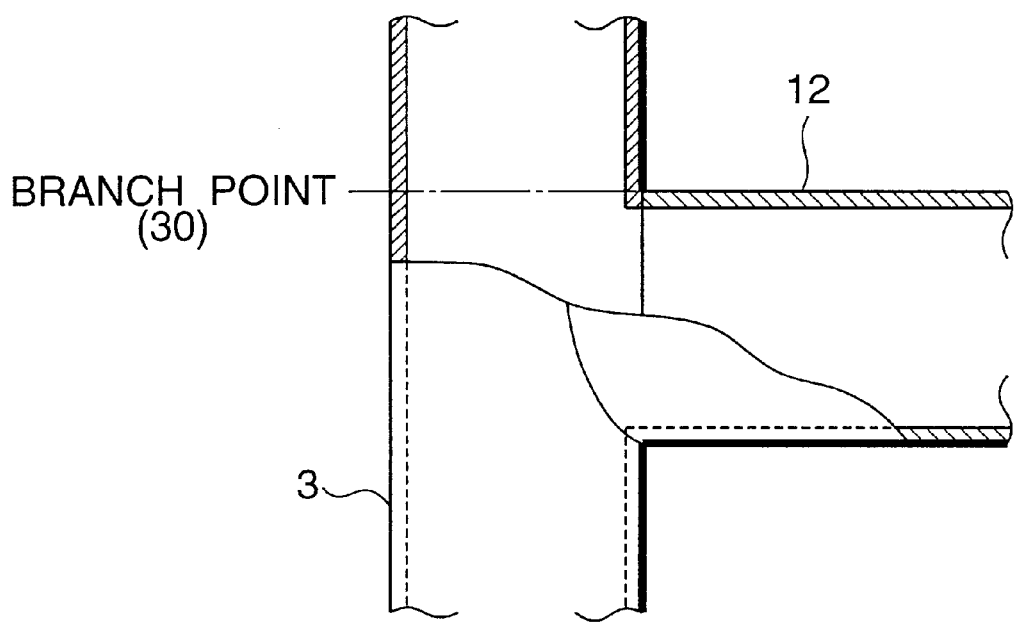
FIG. 8 is a vertical cross sectional view of a connecting point of a pipe 3 and a pipe 12.

The combination of the pipe in which the bottoms is flown and the oxygen containing gas supply nozzle is not specifically limited, for example, the oxygen containing gas supply nozzle(s) 22 can be extended from an optional direction through the wall of the pipe 3 and terminating at any point in the pipe 3 such as shown in FIG. 2 and FIG. 6 or connected with the pipe 3 without extended through the wall of the pipe 3. The nozzle(s) 22 is connected to any suitable source of supply for oxygen containing gas.

In the present invention, known or conventional polymerization inhibitors can also be employed. Such polymerization inhibitors include, but are not limited to, hydroquinone, hydroquinone monomethyl ether, phenothiazine, diphenylamine, copper dialkyldithiocarbamates, and N-oxyl compounds.

According to the invention, the point(s) of adding the polymerization inhibitor(s) is not specifically limited, for example, the polymerization inhibitor being dissolved in the liquid can be added to the distillation column 1 from the top of the column and/or the middle of the column, thereby the addition of polymerization inhibitor to the bottoms may be unnecessary, or the polymerization inhibitor may be added to the pipe 3 and/or reboiler 2 with/without the oxygen containing gas.

In addition to the supply of the oxygen containing gas as described above, at least part of, preferably all of, the inside surfaces of the reboiler 2, should preferably have a surface roughness of 12.5S or less, and more preferably 3.2S or less. By this configuration, the formation of polymer which will adhere to the inner surface of tubes of the reboiler 2 can further effectively be prevented.

Also inner surfaces of the pipe 3 connecting the distillation column 1 with the reboiler 2, and of the pipe 13 connecting the reboiler 2 with the distillation column 1 should preferably have a surface roughness of 12.5S or less, and more preferably 3.2S or less to prevent the formation of polymer of pipe effectively.

The term "the inside surfaces of the reboiler" herein include the region between the inlet of the reboiler and the outlet of the reboiler. The portion of the inside surface of the reboiler where the bottoms turns to the gas-liquid phase preferably satisfy the above mentioned value to efficiently prevent the polymerization.

The term "surface roughness" and "S" used herein are defined in Japanese Industrial Standards (JIS) B0601-1982 (Definitions and Designation of Surface Roughness). The "S" stands for the maximum value of the maximum high.

Polishing means for ensuring the inside surfaces to have a smoothness within the above range are not critical and include mechanical polishing, electrolytic polishing, and other polishing techniques. For example, buffing can be performed using a buff of #200 or more, preferably #300 or more, and more preferably #400 or more.

According to the invented process, the formation of polymerization products in a multitubular reboiler can be effectively prevented and the stable purification of (meth) acrylic acid or its ester by distillation can be effectively attained.

The invention will be further illustrated in detail with reference to several inventive examples and comparative examples below which are not intended to limit the scope of the invention.

EXAMPLE 1

In this example, a distillation column having 1.2 m in column diameter with 20 flat perforated plate trays was used, and the distillation column included a horizontal multitubular reboiler (inside diameter of tubes: 30 mm, length of tubes: 4000 mm, number of tubes: 70). Inside the tubes of the reboiler, a liquid mixture was to pass in a forced circulation system. As the liquid mixture, a crude butyl acrylate containing butyl butoxypropionate and other high boiling impurities (containing 97.5% of butyl acrylate, 1.8% of butyl butoxypropionate, and 0.7% of other components) was fed to the bottom of the column at a rate of 4700 kg/hr. Butyl acrylate, an overhead product, was fed from the top at a reflux ratio of 0.3 (operation pressure: 70 hPa). A purified butyl acrylate containing no high boiling impurity was drawn from the top at a rate of 4500 kg/hr and a butyl acrylate mixture containing concentrated high boiling impurities was drawn from the bottom at a rate of 200 kg/hr. In this procedure, a polymerization inhibitor hydroquinone monomethyl ether was added to the refluxed mixture in a proportion of 150 ppm relative to the fed crude butyl acrylate, and air was continuously supplied from the upstream of an inlet side tube sheet of the multitubular reboiler against the direction of the liquid mixture in a pipe connecting the distillation column with the multitubular reboiler. The proportion of supplied air was 0.2 parts by volume in terms of oxygen relative to the volume at standard temperature and pressure of a vapor evolved in the reboiler. After this purification procedure was continued for 60 days, inside of the distillation column and the reboiler was inspected to find no polymerization product.

Comparative Example 1

The purification procedure of Example 1 was performed for 60 days, except that the air was supplied from downstream of an outlet side tube sheet of the reboiler, and the inside of the distillation column and the reboiler was then inspected. Although no formation of polymerization products was found in the distillation column, 10 tubes of all the 70 tubes of the reboiler were clogged by polymerization products.

EXAMPLE 2

In this example, a distillation column having 1.8 m in column diameter with 40 flat perforated plate trays was employed, and the distillation column comprised a vertical multitubular reboiler (inside diameter of tubes: 30 mm, length of tubes: 4000 mm, number of tubes: 310). Inside the tubes of the reboiler, a liquid mixture was to pass in a natural circulation system. Separately, an aqueous acrylic acid solution was prepared by allowing water to absorb acrylic acid from a reaction gas containing acrylic acid, which reaction gas was formed by the gaseous phase catalytic oxidation of propylene. The aqueous acrylic acid solution contained 65% of acrylic acid, 2% of acetic acid, 31% of water, and 2% of other components and was fed to 20th tray of the distillation column at a rate of 6300 kg/hr. An azeotropic solvent, methyl isobutyl ketone, was fed from the top of the column at a rate of 8500 kg/hr. During this operation, water was separated as an overhead product, and a crude acrylic acid was recovered from the bottom at a rate of 4300 kg/hr (operation pressure: 150 hPa). In this procedure, 200 ppm of hydroquinone and 100 ppm of phenothiazine relative to the fed aqueous acrylic acid solution were added to the refluxed mixture, and oxygen was supplied from two points, in a pipe for supplying the fluid from the bottom of the distillation column to the multitubular reboiler and in the upstream of an inlet side tube sheet of the reboiler. The proportion of the supplied oxygen (total of the oxygen supplied from the two points) was 1 part by volume relative to the volume at standard temperature and pressure of a vapor evolved in the reboiler. In this connection, the inside surface of the pipe connecting between the distillation column and the reboiler, tube sheets and inside surfaces of the reboiler, and of the tubes of the reboiler had been subjected to buffing (#400) to reduce the surface roughness to 3.2 S or less. The purification procedure was continued for 90 days, and the inside of the distillation column, the reboiler, and the pipe connecting the distillation column with the reboiler was inspected to find no polymerization product.

Comparative Example 2

The procedure of Example 2 was performed for 90 days, except that the oxygen was supplied from the bottom of the distillation column, and the inside of the distillation column, the reboiler, and the pipe connecting between the distillation column and the reboiler was inspected. Although no formation of polymerization products was found in the polymerization products clogged 42 tubes of all the 310 tubes of the reboiler, and the polymerization products were attached to the inside of the pipe connecting the distillation column with the multitubular reboiler.

Other embodiments and variations will be obvious to those skilled in the art, and this invention is not to be limited to the specific matters stated above.

What is claimed is:

1. A process for the purification of (meth)acrylic acid, its ester, or both using a distillation unit, said distillation unit comprising a distillation column, a multitubular reboiler, and a pipe connecting said distillation column with said multitubular reboiler, comprising:

feeding a liquid mixture containing (meth)acrylic acid, its ester or both into said distillation column and subjecting the mixture to distillation, feeding a fraction of the liquid mixture from the bottom of said distillation column to said reboiler through the pipe connecting said distillation column with said reboiler, supplying an oxygen containing gas to the fraction of the liquid mixture in at least one region of said pipe between said distillation column and an inlet of said reboiler and/or in at least one region of said reboiler between said inlet and an inlet tube sheet of said reboiler, and feeding the resultant fraction of the liquid mixture back to said distillation column, wherein the formation of polymerization products in said reboiler are reduced.

2. A process according to claim 1, wherein said oxygen containing gas is supplied in a proportion of 0.01 to 5 parts by volume in terms of oxygen relative to the volume at standard temperature and pressure of a vapor evolved in the multitubular reboiler.

3. A process according to claim 2, wherein at least part of an inside surface of said multitubular reboiler has a surface roughness of 12.5 S or less.

4. A process according to claim 2, wherein at least part of the pipe connecting the multitubular reboiler with the distillation column has a surface roughness of 12.5 S or less.

5. A process according to claim 1, wherein at least part of an inside surface of said multitubular reboiler has a surface roughness of 12.5 S or less.

6. A process according to claim 5, wherein at least part of the pipe connecting the multitubular reboiler with the distillation column has a surface roughness of 12.5 S or less.

7. A process according to claim 1, wherein at least part of the pipe connecting the multitubular reboiler with the distillation column has a surface roughness of 12.5 S or less.

8. A process for the purification of (meth)acrylic acid, its ester, or both using a distillation unit, said distillation unit comprising a distillation column, a multitubular reboiler, a pipe connecting said distillation column with said multitubular reboiler and a circulation pump comprising:

feeding a liquid mixture containing (meth)acrylic acid, its ester or both into said distillation column and subjecting the mixture to distillation, feeding a fraction of the liquid mixture from the bottom of said distillation column to said reboiler through the pipe connecting said distillation column with said reboiler, supplying an oxygen containing gas to the fraction of the liquid mixture in at least one region of said pipe between an outlet of said circulation pump and an inlet of said reboiler and/or in at least one region or said reboiler between said inlet and an inlet tube sheet of said reboiler, and feeding the resultant fraction of the liquid mixture back to said distillation column, wherein the formation of polymerization products in said reboiler are reduced.

9. A process according to claim 8, wherein said oxygen containing gas is supplied in a proportion of 0.01 to 5 parts by volume in terms of oxygen relative to the volume at standard temperature and pressure of a vapor evolved in the multitubular reboiler.

10. A process according to claim 9, wherein at least part of an inside surface of said multitubular reboiler has a surface roughness of 12.5 S or less.

11. A process according to claim 9, wherein at least part of the pipe connecting the multitubular reboiler with the distillation column has a surface roughness of 12.5 S or less.

12. A process according to claim 8, wherein at least part of an inside surface of said multitubular reboiler has a surface roughness of 12.5 S or less.

13. A process according to claim 12, wherein at least part of the pipe connecting the multitubular reboiler with the distillation column has a surface roughness of 12.5 S or less.

14. A process according to claim 8, wherein at least part of the pipe connecting the multitubular reboiler with the distillation column has a surface roughness of 12.5 S or less.

* * * * *